United States Patent [19]

Wall

[11] Patent Number: 4,502,161
[45] Date of Patent: Mar. 5, 1985

[54] PROSTHETIC MENISCUS FOR THE REPAIR OF JOINTS

[76] Inventor: W. H. Wall, 2300 Henderson Mill, Atlanta, Ga. 30345

[21] Appl. No.: 524,474

[22] Filed: Aug. 19, 1983

Related U.S. Application Data

[63] Continuation of Ser. No. 303,826, Sep. 21, 1981, abandoned.

[51] Int. Cl.³ .............................................. A61F 1/24
[52] U.S. Cl. ........................................ 3/1.91; 3/1.911; 3/1.912; 128/92 C
[58] Field of Search ................................ 3/1.9–1.913; 128/92 C, 92 CA

[56] References Cited

U.S. PATENT DOCUMENTS

| | | | |
|---|---|---|---|
| 3,178,728 | 4/1965 | Christensen | 3/1.91 |
| 3,579,643 | 5/1971 | Morgan | 128/92 C X |
| 3,867,728 | 2/1975 | Stubstad et al. | 128/92 C X |
| 3,879,767 | 4/1975 | Stubstad | 128/92 C X |
| 3,886,600 | 6/1975 | Kahn et al. | 3/1.91 |
| 3,938,198 | 2/1976 | Kahn et al. | 128/92 C X |
| 3,987,499 | 10/1976 | Scharbach et al. | 3/1.91 |
| 3,992,725 | 11/1976 | Homsy | 3/1.9 X |
| 4,085,466 | 4/1978 | Goodfellow et al. | 3/1.91 |
| 4,129,470 | 12/1978 | Homsy | 156/158 |
| 4,224,696 | 9/1980 | Murray et al. | 3/1.911 |
| 4,224,697 | 9/1980 | Murray et al. | 3/1.911 |
| 4,344,193 | 8/1982 | Kenny | 3/1.911 |

FOREIGN PATENT DOCUMENTS

| | | | |
|---|---|---|---|
| 1122634 | 5/1956 | France | 128/92 C |
| 1340451 | 12/1973 | United Kingdom | 3/1.91 |
| 637118 | 12/1978 | U.S.S.R. | 3/1.9 |

OTHER PUBLICATIONS

"Proplast, Temporomandibular Joint Condylar Prostheses" by Vitek, Inc., Technology for Life (1982).
"Proplast, Implant Material Sheeting and Laminates of Sheeting to Teflon or Silicone Rubber" by Vitek, Inc., Technology for Life (1982).

Primary Examiner—Ronald L. Frinks
Attorney, Agent, or Firm—Eric P. Schellin

[57] ABSTRACT

A prosthetic meniscus replaces the natural meniscus and is located between the natural articular surfaces of the bones of a joint. The prosthetic meniscus includes a body portion formed of a resilient material and further defines an extra-articular extension which is attached to the surface of the bone outside the joint. A reinforcing fabric or mesh is embedded in the resilient material to give the meniscus strength and shape. A meniscus according to the invention allows full articulation of the joint and provides the cushioning and lubricating functions of a natural meniscus while avoiding problems associated with total joint replacements.

13 Claims, 12 Drawing Figures

U.S. Patent   Mar. 5, 1985   Sheet 1 of 3   4,502,161
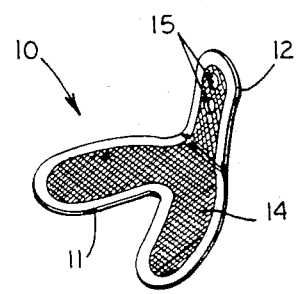
Fig_1
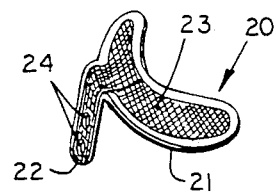
Fig_2
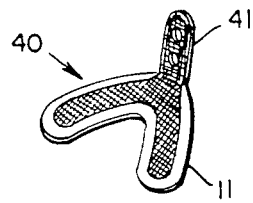
Fig_3
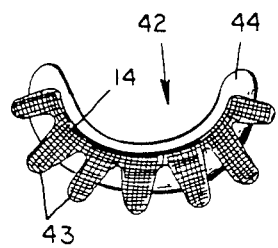
Fig_4
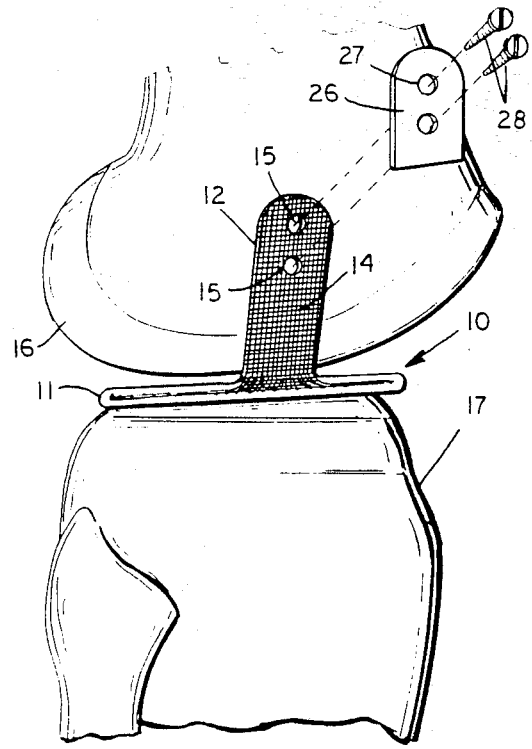
Fig_5
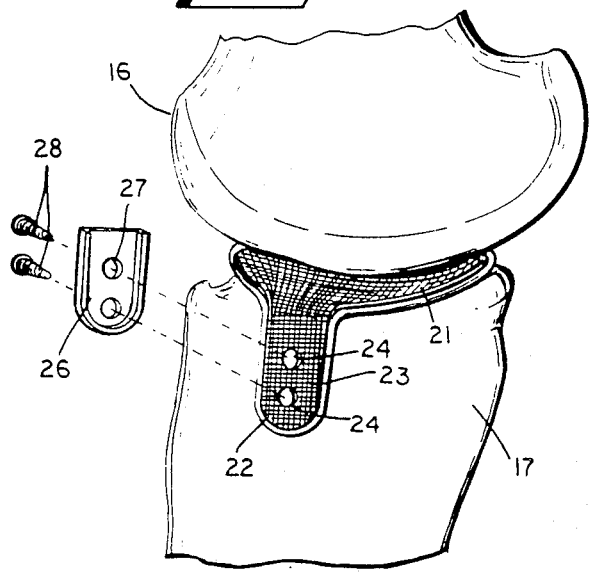
Fig_6

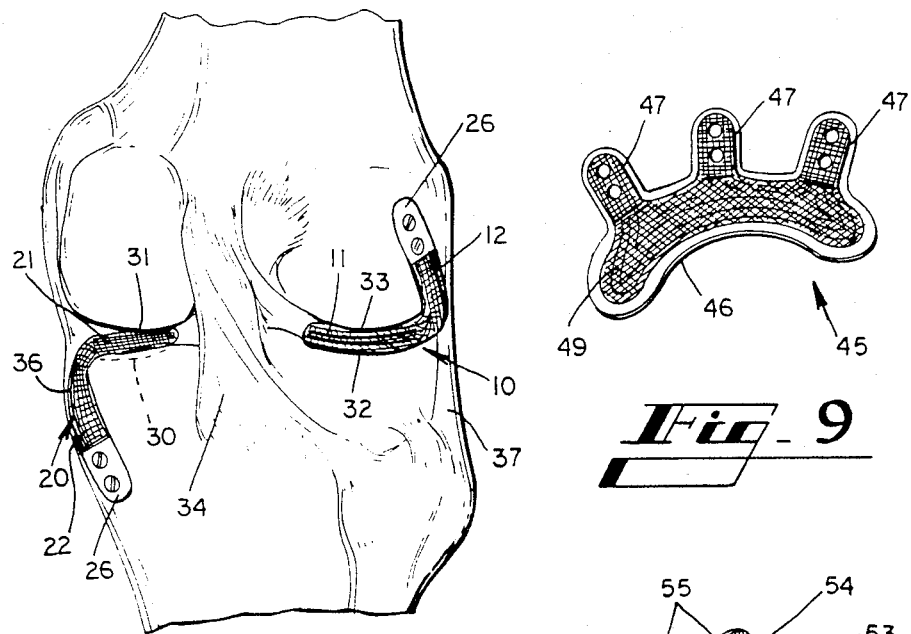
Fig. 7
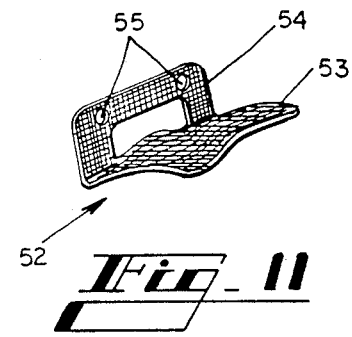
Fig. 9
Fig. 11
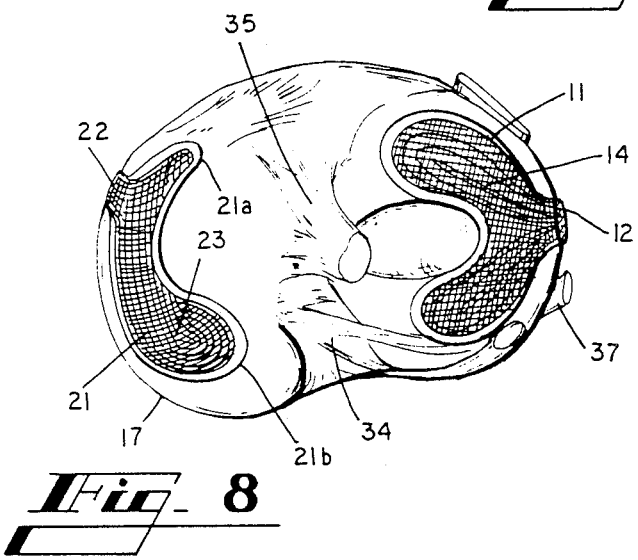
Fig. 8

U.S. Patent   Mar. 5, 1985   Sheet 3 of 3   4,502,161
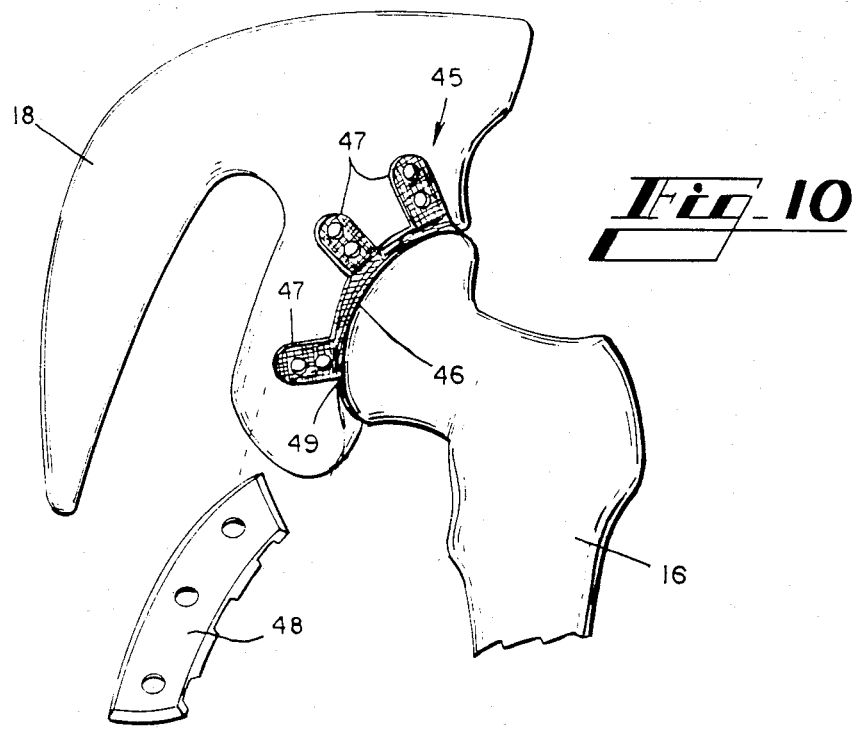
Fig_10
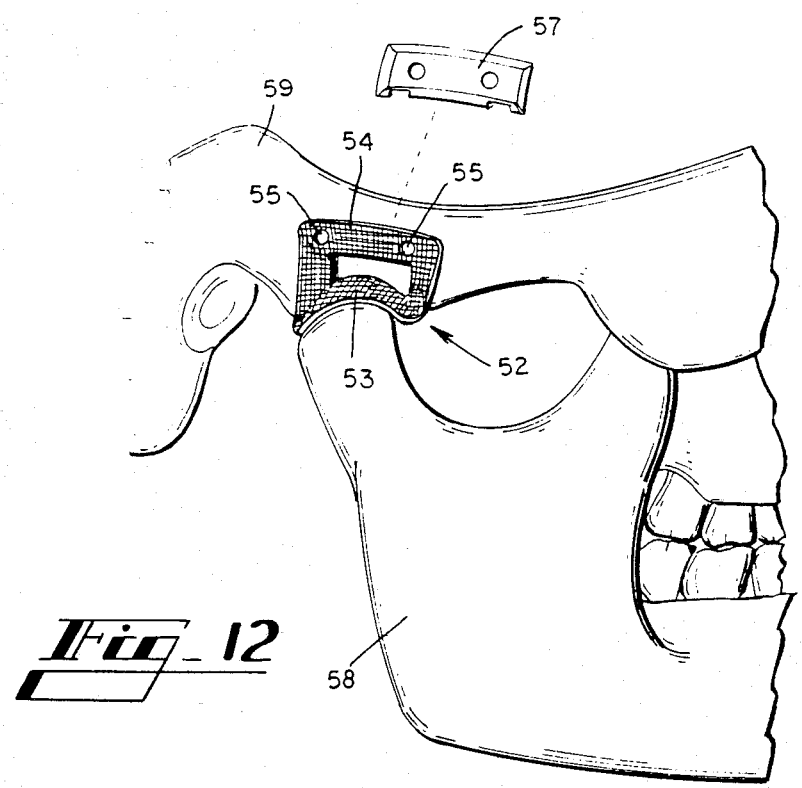
Fig_12

PROSTHETIC MENISCUS FOR THE REPAIR OF JOINTS

This application is a continuation, of application Ser. No. 303,826, filed Sept. 21, 1981, now abandoned.

TECHNICAL FIELD

The present invention relates to prosthetic devices for repairing damaged joints in animals and humans, and more particularly relates to a prosthetic substitute for the natural meniscus or cartilage found in such joints.

BACKGROUND ART

The general function of the meniscus or cartilage which separates the bones of the joint is to cushion and lubricate the joint. When the natural meniscus is damaged as the result of traumatic injury or deterioration, the natural meniscus is often removed surgically. In the absence of the meniscus, the bones of the joint are not properly positioned, cushioned or lubricated. Therefore stresses arise in the operation of the joint, the range of motion and flexibility of the joint can be restricted, and arthritis commonly develops in the joint.

In response to the problems which arise from the mere removal of the natural meniscus, total joint replacements have been proposed. As shown in U.S. Pat. Nos. 4,085,466; 4,224,696 and 4,224,697, such prosthetic joints generally include replacement of the articular surfaces of the bones as well as provision of a mechanical joint or other interface between the artificial articular surfaces. Such total joint replacements are subject to failure of the components or weakening of the bond between the bone and the implanted articular surfaces, and experience has shown that 20-30% of such replacements are ultimately unsuccessful. Furthermore, attempts to provide complete natural movement of joints such as the knee have led to the development of highly complex artificial joints.

U.S. Pat. No. 4,085,466 also suggests that a meniscal component can be made from a resilient plastic material and inserted alone between the natural femoral and tibial articular surfaces. It is further suggested that differential resilience be achieved in such an insert by making the insert in the shape of a disc and wrapping a sock of nylon or other synthetic fiber around the circumferential surface of the disc. However, no means is suggested for holding the disc in place within the joint.

Thus, there is a need in the art for a successful manner in which to avoid the problems of cartilage removal without resort to the complexity and post-operative complications of total joint replacement.

SUMMARY OF THE INVENTION

The present invention fills an important need in the art by providing a novel prosthetic meniscus designed to replace only the natural meniscus and to bear against the natural articular surfaces of the bones of the joint. Generally described, a prosthetic meniscus embodying the present invention comprises a resilient insert shaped to be received within the joint, and reinforcing means embedded within the insert. The prosthetic meniscus of the present invention preferably further comprises an extra-articular extension of the reinforcing material, either alone or embedded in the resilient material, and means for attaching the extension to a bone surface outside the joint. Portions of the reinforcing material can extend outwardly from the exterior of the insert within the joint for attachment of the insert to ligaments which encapsulate the joint.

The resilient insert is preferably shaped to match the form of the natural meniscus, and is preferably constructed of a resilient plastic material such as silicone rubber, or Teflon. However, natural materials such as rubber might be appropriate for some joints. The reinforcing material preferably comprises a tightly woven mesh of stainless steel or nylon strands. The extra-articular extension can be protected with a stainless steel cover and attached to the bone surface outside the joint by means of screws passing through the cover and the extension. The reinforcing mesh strengthens the meniscal insert, helps to maintain the basic shape of the insert while permitting a degree of resilient deformation thereof, prevents tearing of the insert, and provides a strong bond between the intra-articular insert and its extra articular extension which is attached to the bone.

A prosthetic meniscus embodying the present invention is intended to be constructed in various shapes to replace the natural meniscus of any joint, including, but not limited to, the knee, hip, elbow, shoulder, jaw, fingers and even the spine.

Thus, it is an object of the present invention to provide a novel prosthetic meniscus for replacement of the natural meniscus of a joint.

It is a further object of the present invention to provide a prosthetic meniscus capable of replacing a natural meniscus without affecting the extent and types of movement of the joint, and capable of providing the cushioning and lubricating functions of a natural meniscus.

It is a further object of the present invention to provide a prosthetic meniscus that can be inserted into a joint for cooperation with the natural articular surfaces of the bones of the joint.

It is a further object of the present invention to provide a prosthetic meniscus for insertion into a joint, the position of the meniscus being maintained to prevent undesirable dislocation of the meniscus during articulation of the joint.

Other objects, features and advantages of the present invention will become apparent upon reading the following detailed description of embodiments of the invention, when taken in conjunction with the drawing and the appended claims.

BRIEF DESCRIPTION OF THE DRAWING

FIG. 1 is a pictorial view of a prosthetic meniscus embodying the present invention for use in the lateral portion of a knee joint.

FIG. 2 is a pictorial illustration of a prosthetic meniscus embodying the present invention for use in the medial portion of a knee joint.

FIG. 3 is a pictorial illustration of a prosthetic meniscus of the type shown in FIG. 1, showing an alternate embodiment wherein the extra-articular extension is formed of only the reinforcing material.

FIG. 4 is a bottom plan view of a prosthetic meniscus of the type shown in FIG. 1, including projections of the reinforcing material outside the prosthetic meniscus for attachment to adjacent ligaments, soft tissues, or both.

FIG. 5 is a lateral plan view of a knee joint fitted with a prosthetic meniscus embodying the present invention.

FIG. 6 is a medial view of the knee joint of FIG. 5.

FIG. 7 is a rear view of the knee joint of FIGS. 5 and 6, showing some ligaments.

FIG. 8 is a top plan view of the tibial portion of the knee joint of FIGS. 5–7, the femur being removed to expose interior detail.

FIG. 9 is a pictorial illustration of a prosthetic meniscus embodying the present invention for use in a hip joint.

FIG. 10 is a front plan view of a hip joint fitted with a prosthetic meniscus of the type shown in FIG. 9.

FIG. 11 is a pictorial illustration of a prosthetic meniscus embodying the present invention for use in the temporo-mandibular joint.

FIG. 12 is a side plan view of a temporo-mandibular joint fitted with a prosthetic meniscus of the type shown in FIG. 11.

DETAILED DESCRIPTION

Referring now in more detail to the drawing, in which like numerals represent like parts throughout the several views, FIGS. 1, 2 and 5–8 show an embodiment of a prosthetic meniscus according to the invention mounted in a knee joint. Since a knee joint has two menisci, two prosthetic menisci embodying the invention are also provided. FIG. 1 shows a lateral prosthetic meniscus 10 embodying the invention, including an intra-articular body or insert portion 11 formed of a resilient material and shaped to match the shape of the natural meniscus that it replaces. The meniscus 10 further defines an extra-articular extension or strut 12 designed to extend outside of the joint for attachment to the surface of the femur. Embedded within the body 11 and strut 12 of the meniscus 10 is a continuous reinforcing material 14. The resilient material of the meniscus 10 can comprise one of several materials having somewhat differing characteristics. Silicone rubber having a slick surface is sufficiently resilient and movable with respect to the articular surfaces of the bone to provide the desired cushioning and lubricating functions. Silastic material is a suitable silicone rubber. Polytetrafluoroetheylene (marketed under the trademark Teflon) can be deformed to a lesser degree than the materials previously mentioned, but has good lubricative qualities and is suitable where the natural meniscus is thin such as in the temporo-mandibular joint of the jaw. Other materials exhibiting some degree of resiliency, such as natural rubber or silicone rubber surgical foams used for bone rebuilding, could be useful to form prosthetic menisci for particular joints.

The body 11 can be provided with openings passing therethrough for receiving scar tissue, such that the scar tissue assists in securing the body 11 in position within a joint.

The reinforcing material 14 is preferably a closely-woven fine fabric mesh of stainless steel or nylon, Dacron or rayon strands. Other stranded material of similar strength could be used. When the fabric or mesh is embedded in the resilient material, such as by casting or molding a meniscus with the fabric held in place at the center of the molds, the resilient material extends through the openings between strands of the fabric to prevent separation of the resilient material from the fabric. Alternately, a sheet of reinforcing material having some flexibility but being more rigid than the resilient material of the body 11 could be embedded therein. Such a sheet would preferable be perforated to allow the resilient material to pass through the perforations. The strut 12 defines a pair of openings 15 therein to enable the strut 12 to be attached to the bone.

FIG. 5 shows a lateral plan view of the knee joint, and shows the lateral prosthetic meniscus 10 mounted with respect to the joint. The body 11 of the meniscus 10 is positioned between the natural articular surfaces of the femur 16 and the tibia 17. The strut 12 extends laterally out of the joint and upward along the side of the femur 16. Preferably, in attaching the strut 12, a groove is formed in the surface of the femur to receive the strut 12 so that it can be mounted flush with the surrounding bone surface. A stainless steel cover 26 defines a pair of holes 27 therein positioned to mate with the holes 15 of the strut 12. In attachment of the strut 12 to the femur, surgical screws 28 are inserted through the holes 27 and 15 and into the bone.

A medial prosthetic meniscus 20 for use in the knee joint is shown in FIG. 2. The meniscus 20 is similar in construction to the meniscus 10, and includes a body portion 21, a strut 22, reinforcing material 23 embedded therein, and a pair of attachment holes 24 in the strut. It will be noted that the shape of the body portion 21 is different from that of the body portion 11 of the meniscus 10, because the shape of the natural medial meniscus differs from that of the natural lateral meniscus. FIG. 6 shows the medial prosthetic meniscus 20 mounted in the medial portion of the knee joint shown in FIG. 5. The strut 22 extends downwardly and is attached to the surface of the tibia in the same fashion that the strut 12 was attached to the surface of the femur.

FIGS. 7 and 8 further show the positioning of the prosthetic menisci 10 and 20 in the knee joint. FIG. 7 is a rear plan view of the joint showing the menisci 10 and 20 in position between the articular surfaces of the femur 16 and the tibia 17. The lateral prosthetic meniscus 10 lies between the lateral articular surfaces 32 and 33 of the tibia and femur, respectively. The prosthetic meniscus 20 lies between the medial articular surfaces 30 and 31 of the tibia and femur, respectively. It will be noted that insertion of the menisci 10 and 20 does not necessitate significant relocation of any of the ligaments of the knee. Therefore, the central ligaments such as the posterior cruciate ligament 34 and the anterior cruciate ligament 35 are left to perform their functions in the normal manner. Furthermore, outer ligaments such as the medial ligament 36 and the lateral ligament 37 remain in their normal positions to form the joint capsule and assist in holding the menisci 10 and 20 in the proper position. FIG. 8 is a top plan view of the superior surface of the tibia, showing placement of the prosthetic menisci 10 and 20. FIG. 8 shows how the body portions 11 and 21 of the menisci 10 and 20 are shaped to engage the articular surfaces of the tibia. It can be seen from FIGS. 7 and 8 in particular that replacement of the natural menisci by the prosthetic menisci 10 and 20 allows full natural articulation of the knee joint and also provides the cushioning and lubricating function provided by the natural menisci.

FIG. 3 shows an alternate embodiment of a lateral prosthetic meniscus 40 in which the strut 41 for extra-articular attachment of the meniscus 40 is not embedded in the resilient material that forms the body portion 11. The strut 41 can also be embedded in a very thin layer of the resilient material.

FIG. 4 shows another alternate embodiment of a lateral prosthetic meniscus 42 for a knee joint. In the meniscus 42, loops formed by strands of the reinforcing material 14 extend horizontally outwardly beyond the surface of the body portion 44. Such loops 43 would be primarily located around the outer side of the meniscus and would be used to suture the meniscus 42 to adjacent ligaments, soft tissue or both. It should be understood that the modifications described in connection with the lateral prosthetic menisci 40 and 42 can be readily utilized in a medial meniscus for the knee or for a meniscus designed for any other joint. It will be further understood that in the case of a reinforcing mesh embedded entirely within the body portion, sutures can be inserted through peripheral areas of the body portion and through the embedded mesh to secure the meniscus to adjacent ligaments or soft tissue.

A prosthetic meniscus 45 for a hip joint is shown in FIG. 9. The meniscus 45 includes a body 46 and a plurality of struts 47 extending therefrom for extra-articular attachment of the meniscus 45 to the ilium 18. The meniscus 45 is constructed in a manner generally similar to the knee joint menisci 10 and 20 described hereinabove and includes a reinforcing mesh 49. FIG. 10 is plan view of the hip joint showing the meniscus 45 positioned between the ilium 18 and the femur 16. The struts 47 are attached to the ilium in the same manner as the struts 12 and 22 of the knee joint are attached to the bones of the knee. Since the struts are adjacent to one another, a continuous stainless steel cover 48 can be used to cover all of the struts 47. Alternately, they can be individually covered and attached in the manner described hereinabove.

FIG. 11 shows a prosthetic meniscus 52 designed to replace the natural meniscus of the temporo-mandibular joint. The meniscus 52 includes a body portion 53 constructed of resilient material and an integrally formed U-shaped strut 54 which extends outside the joint. The strut 54 includes at least two openings 55 therein for attachment of the meniscus 52 to the temporal bone. Embedded in the body 53 and strut 54 is a mesh of reinforcing material of the type described above. Again, the shape of the body portion 53 of the meniscus 52 conforms to the shape of the natural meniscus of the temporo-mandibular joint. FIG. 12 is a side plan view of the jaw showing the prosthetic meniscus 52 in place in the temporo-mandibular joint. The body portion 53 of the meniscus 52 lies between the mandible 58 and the temporal bone 59. A stainless steel cover 57 is provided for protection and attachment of the strut 54 in the same manner as described above in connection with other embodiments of the present invention.

Surgical techniques needed to implant a prosthetic meniscus embodying the invention are similar to known techniques for cartilage removal and will be readily understood by those skilled in the art. Attachment using surgical screws required to affix the extra-articular extensions to the bones is a well-known surgical technique.

In addition to the method of attachment of the struts using surgical screws, the struts 12, 22, 41, 47 and 54 can be attached by other means such as adhesive or surgical staples.

It will be seen that the prosthetic meniscus embodying the invention provides a strong meniscal replacement that is retained in proper position and is still able to accomplish the cushioning and lubrication functions of the natural meniscus and to allow the full range of normal movement of the joint. The resilient material comprising the meniscus twists, translates and deforms under the force of the bones of the joint, but returns to its original shape. The reinforcing material assists in shape retention and prevents tearing of the prosthetic meniscus even in situations where a natural meniscus might tear. The extra-articular extension allows the prosthesis to be positively, though not rigidly, located, without interfering with the functioning of the body portion of the prosthesis.

While this invention has been described in detail with particular reference to preferred embodiments thereof, it will be understood that variations and modifications can be effected within the spirit and scope of the invention as described hereinbefore and as defined in the appended claims.

I claim:

1. A prosthetic meniscus for placement within a joint capsule comprising:
    a resilient insert shaped to be received within the joint capsule to provide at least substantially the same area of bearing surface as the natural meniscus and defining an extension thereof for extending outside the joint capsule;
    reinforcing mesh embedded within said resilient insert and integrally extending into said extension; and
    means for fixedly attaching the extending end of said extension to an outer bone surface outside the joint capsule; said extension being connected to said insert so as to permit relative movement between said insert and said extension.

2. The prosthetic meniscus of claim 1, wherein said resilient material comprises silicone rubber.

3. The prosthetic meniscus of claim 1, wherein said resilient insert comprises polytetrafluoroethylene.

4. The prosthetic meniscus of claim 1, wherein said reinforcing mesh comprises a mesh of stainless steel strands.

5. The prosthetic meniscus of claim 1, wherein said reinforcing mesh comprises a mesh of nylon strands.

6. The prosthetic meniscus of claim 1, wherein said reinforcing mesh comprises a fabric.

7. The prosthetic meniscus of claim 1, wherein portions of said reinforcing mesh extend outwardly from the exterior of said resilient insert for attachment to ligaments associated with the joint.

8. The prosthetic meniscus of claim 1, wherein said insert defines openings passing therethrough for receiving scar tissue, such that said scar tissue assists in securing said insert in position in said joint.

9. A prosthetic meniscus for placement in a joint, comprising:
    a resilient insert shaped to be received within the joint;
        reinforcing mesh embedded within said resilient material over an entire cross-section of said insert and exiting said resilient material to form a non-embedded extension for extending outside the joint; and
    means for attaching said extension to an outer bone surface outside the joint.

10. A prosthetic meniscus for insertion into a temporo-mandibular joint, comprising:
    a body portion comprising a resilient plastic material shaped to be received within the joint;
    a generally U-shaped strut of said resilient material attached integrally to said body portion at two locations and adapted to extend out of the joint for attachment to the temporal bone; and
    a one-piece mesh of reinforcing strands embedded within said resilient material and extending integrally from said body portion through said strut.

11. A prosthetic meniscus for placement within a temporomandibular joint capsule comprising:
- a resilient insert shaped to be received within the joint capsule positioned adjacent to the glenoid fossa to provide at least substantially the same area of bearing surface as the natural meniscus and defining an extension thereof for extending outside the joint capsule;
- reinforcing mesh embedded within said resilient insert and integrally extending into said extension; and
- means for fixedly attaching the extending end of said extension to an outer bone surface of the temporal bone outside the joint capsule; said extension being connected to said insert so as to permit relative movement between said insert and said extension.

12. A prosthetic meniscus for placement within a knee joint capsule comprising:
- a resilient insert shaped to be received within the joint capsule to provide at least substantially the same area of bearing surface as the natural meniscus and defining a strut-like extension thereof for extending between ligaments of the joint capsule to outside the joint capsule;
- reinforcing mesh embedded within said resilient insert and integrally extending into said extension; and
- means for fixedly attaching the extending end of said reinforced extension to an outer bone surface outside the joint capsule; said extension being connected to said insert so as to permit relative movement between said insert and said extension.

13. A prosthesis for placement within a hip joint capsule comprising:
- a resilient insert shaped to be received within the joint capsule to provide at least substantially the same area of bearing surface as the natural cartilage and defining at least one strut-like extension thereof for extending between ligaments of the joint capsule to outside the joint capsule;
- reinforcing mesh embedded within said resilient insert and integrally extending into said extension; and
- means for fixedly attaching the extending end of said reinforced extension to an outer bone surface of the ilium bone outside the joint capsule; said extension being connected to said insert so as to permit relative movement between said insert and said extension.

* * * * *

REEXAMINATION CERTIFICATE (1104th)
United States Patent [19]
Wall

[11] B1 4,502,161
[45] Certificate Issued Jul. 25, 1989

[54] PROSTHETIC MENICUS FOR THE REPAIR OF JOINTS

[76] Inventor: William H. Wall, 2300 Henderson Mill, Atlanta, Ga. 30345

Reexamination Request:
No. 90/001,196, Mar. 17, 1987

Reexamination Certificate for:
Patent No.: 4,502,161
Issued: Mar. 5, 1985
Appl. No.: 524,474
Filed: Aug. 19, 1983

Related U.S. Application Data

[63] Continuation of Ser. No. 303,826, Sep. 21, 1981, abandoned.

[51] Int. Cl.$^4$ ............... A61F 2/30; A61F 2/38; A61F 2/32
[52] U.S. Cl. ................. 623/18; 623/20; 623/22; 128/92 R
[58] Field of Search .................. 623/16-23

[56] References Cited

U.S. PATENT DOCUMENTS

| | | | |
|---|---|---|---|
| 3,178,728 | 4/1965 | Christensen | 3/1.91 |
| 3,579,643 | 5/1971 | Morgan | 128/92 |
| 3,867,728 | 2/1975 | Stubstad et al. | 128/92 |
| 3,879,767 | 4/1975 | Stubstad | 128/92 |
| 3,886,600 | 6/1975 | Kahn et al. | 3/1.91 |
| 3,938,198 | 2/1976 | Kahn et al. | 128/92 |
| 3,987,499 | 10/1976 | Scharbach et al. | 3/1.91 |
| 3,992,725 | 11/1976 | Homsy | 3/1.9 |
| 4,052,753 | 10/1977 | Dedo | 3/1 |
| 4,085,466 | 4/1978 | Goodfellow et al. | 3/1.91 |
| 4,129,470 | 12/1978 | Homsy | 156/158 |
| 4,224,696 | 9/1980 | Murray et al. | 3/1.911 |
| 4,224,697 | 9/1980 | Murray et al. | 3/1.911 |
| 4,313,232 | 2/1982 | Habal et al. | 3/1.91 |
| 4,344,193 | 8/1982 | Kenny | 3/1.911 |

FOREIGN PATENT DOCUMENTS

| | | | |
|---|---|---|---|
| 1122634 | 9/1956 | France | 623/18 |
| 637118 | 12/1978 | U.S.S.R. | 3/1.9 |
| 1340451 | 12/1973 | United Kingdom | 3/1.91 |

OTHER PUBLICATIONS

Geo. T. Stratigos, "Reconstruction of the TMJ by Permanent Fixation of Silastic to the Temporal Bone," Oral Surgery: Trans. of the IVth Int'l Conf. on Oral Surgery, May 1971.
Robert W. Christensen, "The Correction of Mandibular Ankylosis by Arthroplasty and the Insertion of a Cast Vitallium Glenoid Fossa," J.S.C.S.D.A. 31:177-129, 1963.
Michael S. Freedus et al., "Principles of Treatment for Temporomandibular Joint Ankylosis," Journal of Oral Surgery, 33:757-765, 1975.
John N. Kent et al., "Temporomandibular Joint Condylar Prosthesis: A Ten-Year Report," Journal of Oral and Maxillofacial Surgery, 41:245-254, 1983, Apr.
W. C. Hansen and B. W. Deshazo, "Silastic Reconstruction of TMJ Meniscus," Plastic and Reconstructive Surgery, 43(4): 388-391, 1969.
Vitek Brochure–"Temporomandibular Joint Implants", Jun. 1983.
Vitek Brochure–"Proplast Implant Material: TMJ Condylar Prosthesis," Nov. 1981.
Complaint
Answer
File Wrapper
Grafstein & Schwarz, "Handbook of Technical Devices," 1971.

*Primary Examiner*—Ronald L. Frinks

[57] ABSTRACT

A prosthetic meniscus replaces the natural meniscus and is located between the natural articular surfaces of the bones of a joint. The prosthetic meniscus includes a body portion formed of a resilient material and further defines an extra-articular extension which is attached to the surface of the bone outside the joint. A reinforcing fabric or mesh is embedded in the resilient material to give the meniscus strength and shape. A meniscus according to the invention allows full articulation of the joint and provides the cushioning and lubricating functions of a natural meniscus while avoiding problems associated with total joint replacements.

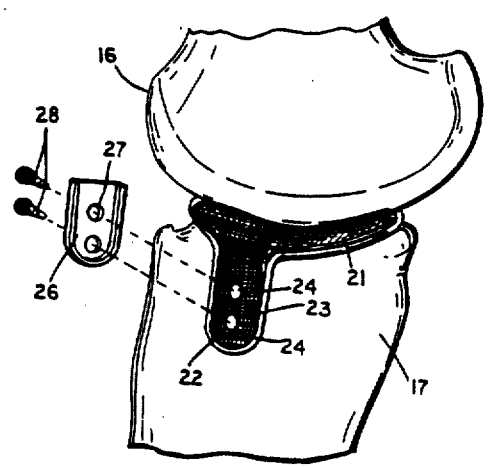

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10, 12 and 13 is confirmed.

Claims 1, 7, 9 and 11 are determined to be patentable as amended.

Claims 2–6 and 8, dependent on an amended claim, are determined to be patentable.

1. A prosthetic meniscus for *replacement of a natural cartilage meniscus between the natural articulating ends of the bones of a joint* [placement] within a joint capsule comprising:
   a resilient insert *having a body portion anatomically shaped to be received between said natural articulating ends of the bones of the joint* within the joint capsule to provide at least substantially the same area of bearing surface *for the ends of the bones of said joint* as the natural meniscus [and defining an extension thereof for extending outside the joint capsule]; *said resilient insert having at least one integral articular extension adapted and constructed to extend outside from between the ends of the bones of the joint of a joint capsule when said resilient insert is in position, said extension having an extending end portion remote from said body portion,*
   reinforcing mesh embedded within said resilient insert and integrally extending into said extension; and
   means for fixedly attaching the extending end of said extension to an outer bone surface outside the joint [capsule]; said extension being connected to said insert so as to permit relative movement between said insert and said extension.

7. The prosthetic meniscus of claim 1, wherein portions of said reinforcing mesh extend outwardly from the [exterior] *body portion* of said resilient insert for attachment to ligaments associated with the joint.

9. A prosthetic meniscus for [placement in] *replacement of a natural cartilage meniscus between the natural articulating ends of the bones of* a joint, comprising:
   a resilient insert *having a body portion anatomically shaped to be received* [within] *between said natural articulating ends of the bones of* the joint;
   reinforcing mesh embedded within said *body portion of said* resilient [material] *insert* over an entire cross-section of *said body portion of* said insert and exiting *said body portion of* said resilient [material] *insert* to form [a] *at least one* non-embedded extension for extending *from between the ends of the bones of the joint* outside the joint; and
   means for attaching said extension to an outer bone surface outside the joint.

11. A prosthetic meniscus for *replacement of a natural cartilage meniscus between the natural articulating ends of the bones of a* placement within a temporomandibular joint capsule comprising:
   a resilient insert *having a body portion anatomically shaped to be received* [within the] *between said natural articulating ends of the bones of the temporomandibular* joint capsule positioned adjacent to the glenoid fossa to provide at least substantially the same area of bearing surface as the natural meniscus [and defining an]; *said resilient insert having at least one integral articular* extension [thereof for extending] *adapted and constructed to extend outside from between the ends of the temporomandibular joint of a* [the] joint capsule *when said resilient insert is in position, said extension having an extending end portion remote from said body portion;*
   reinforcing mesh embedded within said resilient insert and integrally extending into said extension; and
   means for fixedly attaching the extending end *portion* of said extension to an outer bone surface of the temporal bone outside the joint capsule; said extension being connected to said insert so as to permit relative movement between said insert and said extension.

* * * * *